(12) United States Patent
Halliday

(10) Patent No.: US 7,765,860 B2
(45) Date of Patent: Aug. 3, 2010

(54) ROADWAY GRIP TESTER AND METHOD

(76) Inventor: Donald R. Halliday, 5312 Cascade Dr., Powell, OH (US) 43065

( * ) Notice: Subject to any disclaimer, the term of this patent is extended or adjusted under 35 U.S.C. 154(b) by 0 days.

(21) Appl. No.: 12/404,603

(22) Filed: Mar. 16, 2009

(65) Prior Publication Data

US 2009/0173137 A1    Jul. 9, 2009

Related U.S. Application Data

(62) Division of application No. 11/652,274, filed on Jan. 11, 2007, now Pat. No. 7,509,847.

(60) Provisional application No. 60/758,047, filed on Jan. 11, 2006.

(51) Int. Cl.
*G01M 17/02* (2006.01)

(52) U.S. Cl. .............................................. 73/146; 73/9

(58) Field of Classification Search ........................ None
See application file for complete search history.

(56) References Cited

U.S. PATENT DOCUMENTS

| | | | | |
|---|---|---|---|---|
| 4,098,111 A | * | 7/1978 | Hardmark et al. ................. | 73/9 |
| 4,594,878 A | * | 6/1986 | Abe et al. ......................... | 73/9 |
| 4,662,211 A | * | 5/1987 | Strong ............................... | 73/9 |
| 4,909,073 A | * | 3/1990 | Takahashi et al. .............. | 73/146 |
| 4,958,512 A | * | 9/1990 | Johnsen ............................ | 73/9 |
| 5,561,244 A | * | 10/1996 | Olesky et al. .................. | 73/146 |
| 5,851,086 A | * | 12/1998 | Kurasako ...................... | 404/94 |
| 5,900,531 A | * | 5/1999 | Mani et al. ........................ | 73/9 |
| 6,192,736 B1 | * | 2/2001 | Clem ............................... | 73/9 |
| 6,321,586 B1 | * | 11/2001 | Wojtowicz et al. ............... | 73/9 |
| 6,427,519 B2 | * | 8/2002 | Ueda et al. ........................ | 73/9 |
| 6,463,784 B2 | * | 10/2002 | Kashiwagi et al. ............... | 73/9 |

* cited by examiner

*Primary Examiner*—Andre J Allen
(74) *Attorney, Agent, or Firm*—Mueller Smith & Okuley, LLC

(57) ABSTRACT

A method for measuring road surface friction of a road surface uses a vehicle that moves across the road surface wherein (1) an auxiliary independent wheel assembly is towed behind the vehicle and is in contact with the road surface, an auxiliary wheel of the wheel assembly is freely rotatable by movement of the vehicle and is one or more of toed in or toed out with respect to a direction of travel of the vehicle so as to create an isolated axial force on the auxiliary wheel: (2) the axial force on the auxiliary wheel is measured while the vehicle moves across the road surface, and the measured axial force is correlated with the road surface friction. The independent wheel assembly is load isolated from the weight of the towing vehicle and the independent wheel assembly is loaded by placing ballast thereon.

13 Claims, 9 Drawing Sheets

ROADWAY GRIP TESTER AND METHOD

CROSS-REFERENCE TO RELATED APPLICATIONS

This application is a divisional of U.S. patent application Ser. No. 11/652,274, filed Jan. 11, 2007, which claims benefit of U.S. provisional application No. 60/758,047, filed Jan. 11, 2006, the disclosure of which is expressly incorporated herein by reference.

STATEMENT REGARDING FEDERALLY SPONSORED RESEARCH

Not applicable.

BACKGROUND

Disclosed generally is a practical system of measuring road surface friction using an auxiliary wheel and more particularly to a system wherein a switch in the cab deploys the measuring wheel and the in-cab display gives a continuous reading of road surface friction as soon as the wheel rotates. The road friction tester ("RFT") is designed for use in the trucking industry to determine road surface grip where driving conditions may be hazardous.

In U.S. Pat. No. 6,840,098 (the "'098 patent", which is incorporated herein by reference) the original GEM™ device is disclosed to include a vehicle and a device for measuring road surface friction, which device is affixed to the vehicle. The device for measuring road surface friction includes an auxiliary wheel mounted to the vehicle and between the vehicle and the road surface. The auxiliary wheel is toed in or toed out, loaded, and mounted on an axle for its free rolling. A calibrated force sensor is associated with the auxiliary wheel to measure the isolated axial force thereon. A converter displays the road friction and displays it to the vehicle operator or remotely. The GEM™ device is used for measuring road surface friction of a road surface and uses a vehicle that moves across the road surface. An auxiliary independent wheel is interposed between the vehicle and the road surface. The auxiliary wheel is freely rotatable by movement of the vehicle and is toed in or toed out (skewed) with respect to a direction of travel of the vehicle so as to create an axial force on the auxiliary wheel. The axial force on the auxiliary wheel is isolated and measured while the vehicle moves across the road surface. The measured axial force is correlated with the road surface friction.

While such design has been determined to work effectively and efficiently when used in conjunction with a snow plow or other heavy vehicle, a modified design was determined to be needed when the GEM™ device was towed behind or mounted under a small vehicle, such as a SUV, pickup truck, or like light-weight vehicle, such as a passenger vehicle or car.

It is to such lightweight vehicle RFT device (the RT3™ device) that the present invention is based.

BROAD STATEMENT

A method for measuring road surface friction of a road surface uses a vehicle that moves across the road surface wherein (1) an auxiliary independent wheel assembly is towed behind the vehicle and is in contact with the road surface, an auxiliary wheel of the wheel assembly is freely rotatable by movement of the vehicle and is one or more of toed in or toed out with respect to a direction of travel of the vehicle so as to create an isolated axial force on the auxiliary wheel: (2) the axial force on the auxiliary wheel is measured while the vehicle moves across the road surface, and the measured axial force is correlated with the road surface friction. The independent wheel assembly is load isolated from the weight of the towing vehicle and the independent wheel assembly is loaded by placing ballast thereon. A variety of improvements are disclosed which have particular relevance when a normal passenger vehicle (car, light duty truck, or SUV) is used to tow the RGT.

BRIEF DESCRIPTION OF THE DRAWINGS

For a fuller understanding of the nature and advantages of the present invention, reference should be had to the following detailed description taken in connection with the accompanying drawings, in which.

These drawings will be described in further detail below.

DETAILED DESCRIPTION

A. Roadway Grip Tester

While the '098 patent device is a substantial step forward in the art, it became apparent that design changes were required in order to make the device more user friendly to automobile and truck, for example, drivers and in order to reliably measure smaller side forces between a toed wheel and the road surface. It is to such practice device that is disclosed herein.

1. In General

Optionally, the RGT wheel can be towed behind or placed under a small vehicle, as compared to being mounted on a large vehicle like a snowplow. For this to happen the side loads that can be used in this application are significantly lower than with the snowplow type vehicle. This smaller side force is required such that the affects on the smaller vehicle because of the RGT wheel present are reduced. This smaller force is a result of doing two things: (1) placing a smaller vertical load on the wheel and (2) reducing the angle of toe.

2. Ballast Weight & Shock Absorber Use

For the tow hitch type application, when considering the use of a lightweight vehicle particularly, the constant vertical force required for such an application should not be generated from using the vehicle weight in any way, since this will result in a reduction of vertical load at any of the vehicle tires which could result in a dangerous handling condition for that vehicle, especially in low road grip conditions. This can be compensated somewhat by adding ballast to the vehicle; however, the variation in vertical weight on the RGT wheel that ensues with this method would not allow a constant friction measurement between tire and road surface. The solution to this problem is to use ballast weight that can be placed close to the auxiliary wheel center and for this weight to be relatively independent of the vehicle itself. This can be achieved by mounting the auxiliary wheel on a wishbone, as in the under truck model, placing ballast weights on the auxiliary wheel center, and inserting a shock absorber (or shock absorbing system) between the wishbone and the mount frame. The shock absorber allows the auxiliary wheel tire to traverse the road surface smoothly and not result in bouncing of the wheel. This replicates very closely similar conditions as seen by a small vehicle tire. It also is possible that this use of ballast, instead of constant vertical load generated by a hydraulic cylinder, also could be used in the under-truck installation version.

Figure 1:
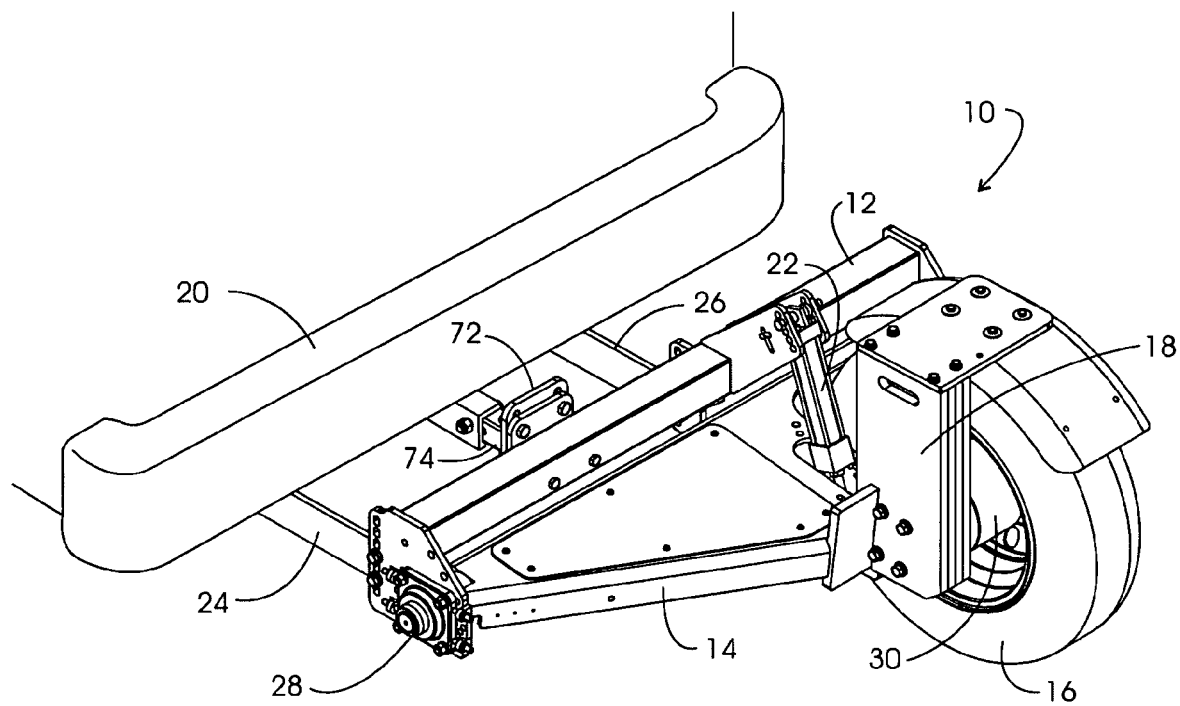
FIG. 1 is a perspective view of the RGT mounted solidly to a lightweight vehicle (pickup truck) using stabilizer plates on each side.

FIG. 1 shows the disclosed RGT, 10, that includes, inter alia, a rigid frame, 12, mounting to the vehicle, a wishbone frame, 14 (see FIG. 3), a wheel/tire assembly, 16, and ballast weight, 18, towed by a vehicle, 20. A shock absorber, 22, accommodates any bounce of the wheel/tire assembly 16 due to rough roads or the like.

3. Rigidly Attached Frame when Using a Single RGT Wheel

Auxiliary wheel assembly 16 requires that the wheel be rigidly attached to the frame of vehicle 20 in order to maintain a consistent toe angle. This is achieved by attaching RGT frame 14 rigidly to vehicle 20 framework by means of stabilizer plates, 24 and 26 (not shown), on either side of the vehicle tow hitch assembly. It also is possible, but less practical, to incorporate the RGT frame as part of the vehicle tow hitch assembly where it can be directly fastened to the vehicle chassis, i.e., the RGT frame replaces the vehicle standard tow hitch frame.

4. Small Side Force on Tow Hitch Version

The affects of the generated RGT side force on vehicle 20 cannot upset vehicle 20 and/or the driver of vehicle 20. This requires that the toe angle of wheel assembly 16 cannot be large, i.e., the tow angle needs to be in the order of about 1 to about 2 degrees relative to the vehicle longitudinal centerline when using a normally available road car tire. It has been determined that the side force generated by auxiliary wheel (RGT) assembly 10 should not be in excess of about 175 lb when vehicle 20 is driven in a straight line. For the road tire chosen, placing the wheel at about 1.5 degrees and using about 300 lb of dead weight (ballast) between the RGT tire and the ground achieves this.

5. Toe Adjustment

Figure 2:
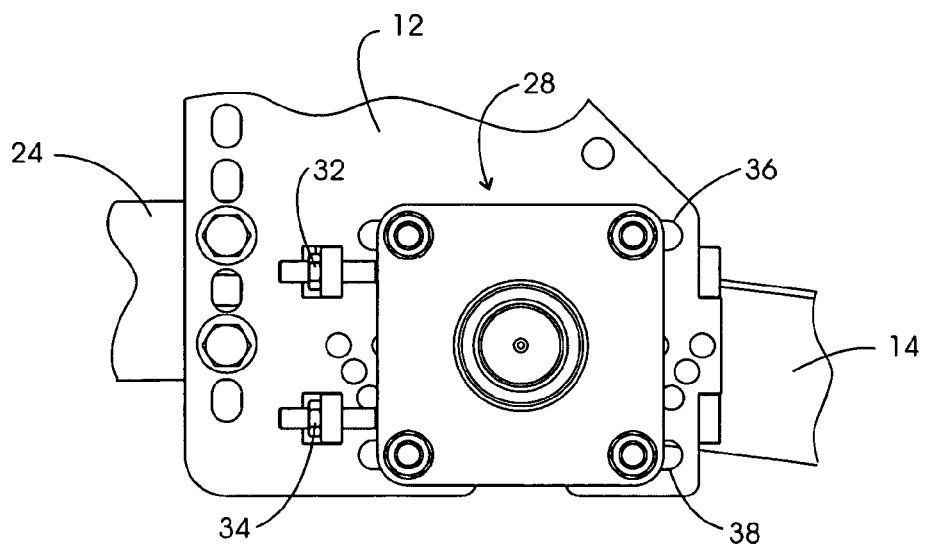
FIG. 2 is a plan view of the RGT showing threaded stops to bearing position to allow fine adjustment of toe angle of the RGT wheel for both the under truck and tow behind versions.

Each vehicle "tracks" slightly differently compared to other vehicles of the same or different type. For this reason, it is necessary, once the RGT wheel has been attached to the vehicle, that it be aligned at the required angle to the towing vehicle in order to generate the desired side force on a selected road surface. This is best achieved in one of two ways. Shims can be placed on either side of the GEM hub bolt faces. These are relatively close at about 10.25" centers and awkward to adjust when all items are bolted to the GEM hub. The more desirable method, as illustrated in FIG. 2, is to, in plan view, rotate the whole wishbone by having the capacity to slide each of the 2 support hub assemblies, 28 and 29 (see FIG. 3 also), mounted at each end of the wishbone fore/aft by undoing and then re-tightening the bearing mount bolts, as for example for support bearing assembly 28, bolts 32 and 34, which permits support bearing assembly 28 to move within a pair of slots, 36 and 38.

6. Swing Arm—Easy Tire Replacement

Figure 3:
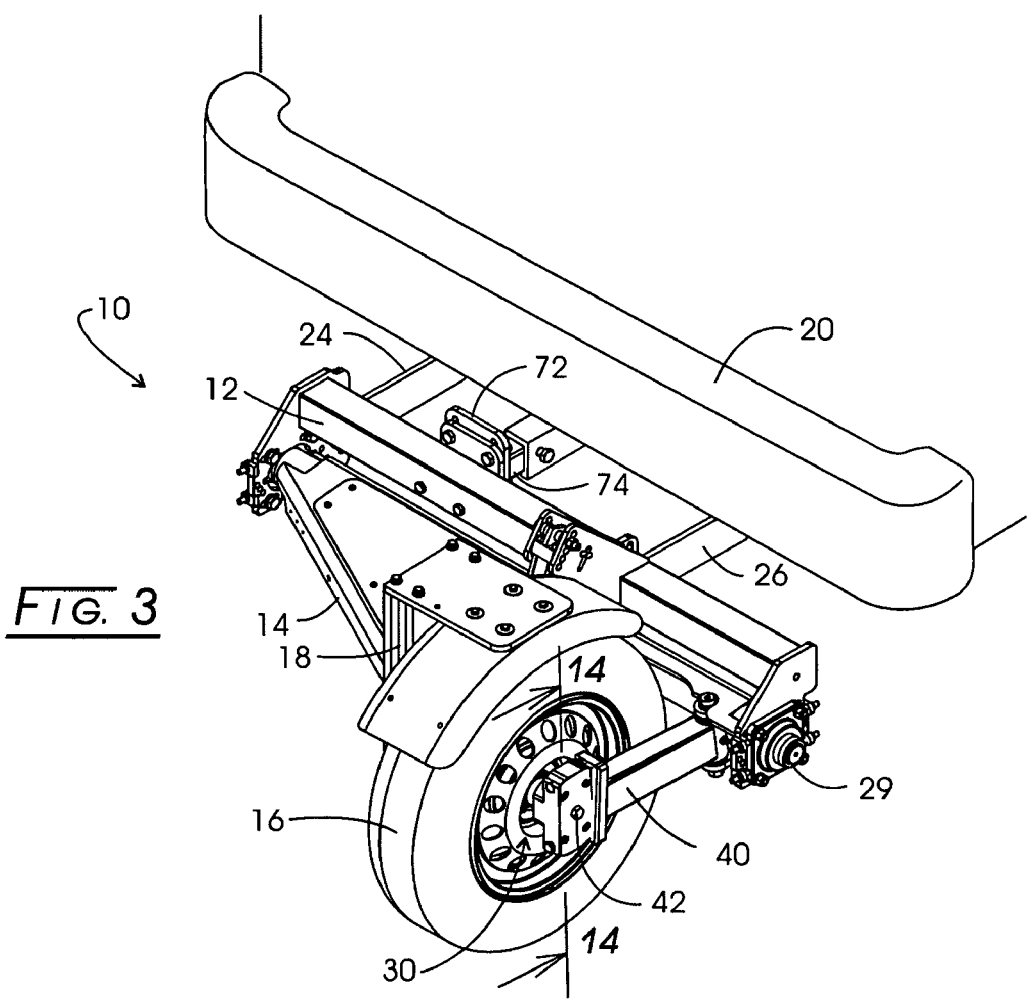
FIG. 3 is an overhead perspective view of the RGT showing the swing arm and swing arm pivot that permits facile changing of the RGT wheel for both the under truck and tow behind versions.

It is desirable to be able to replace wheel/tire assembly 16 readily. Using a cantilevered system or a swing arm, 40, secondary support can do this as illustrated in FIG. 3. A cantilevered system would require some redesign of '098 patent GEM hub to retain its rigidity with respect to wheel position especially in toe control. Swing arm 40 is released by undoing a single bolt at the axle center and then pivots at the pivot center, 42, giving clearance to remove wheel/tire assembly 16.

7. High Resolution Load Cell

To obtain good accuracy and resolution of this force output, the load cell cannot be of a high load value since any repeatability, accuracy, and temperature affects, etc., are as a % of the maximum load cell value. It is, thus, necessary that the load cell maximum load value be as low a possible. Because of this requirement, it is, therefore, very easy to overload the load cell, which has low maximum capacity.

Figure 4:
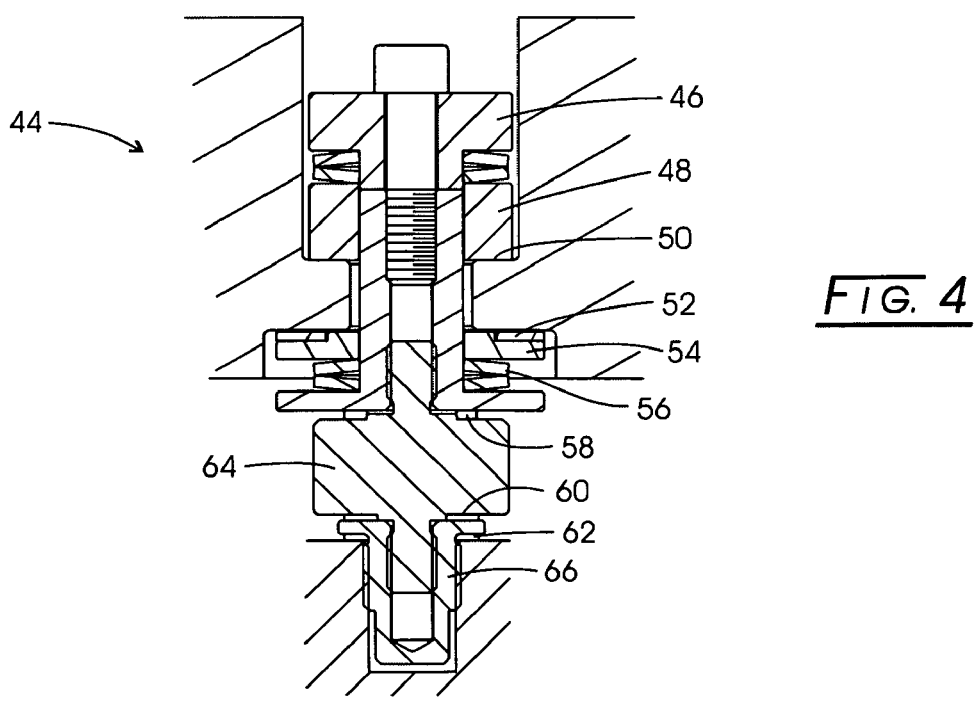
FIG. 4 is a schematic of the load cell and stop layout for both the under truck and tow behind versions.

The load cell and stop layout are illustrated in FIG. 4. Referring initially to the load cell assembly, 44, the components are from top to bottom: a load cell clamp, 46; a load cell bushing, 48, a no load end float gap, 50; an end float shim, 52; a load cell washer, 54; a Bellville load cell spring washer, 56; a face height shim, 58; a load cell recess, 60; and a load cell indexing shim, 62. A load cell, 64, is disposed next with lower load cell bushing, 66, completing the load cell assembly 44. The various bushings and washers can be of the Bellville type, i.e., spring loaded, which along with the stops retard overloading of the load cell.

Figure 14:
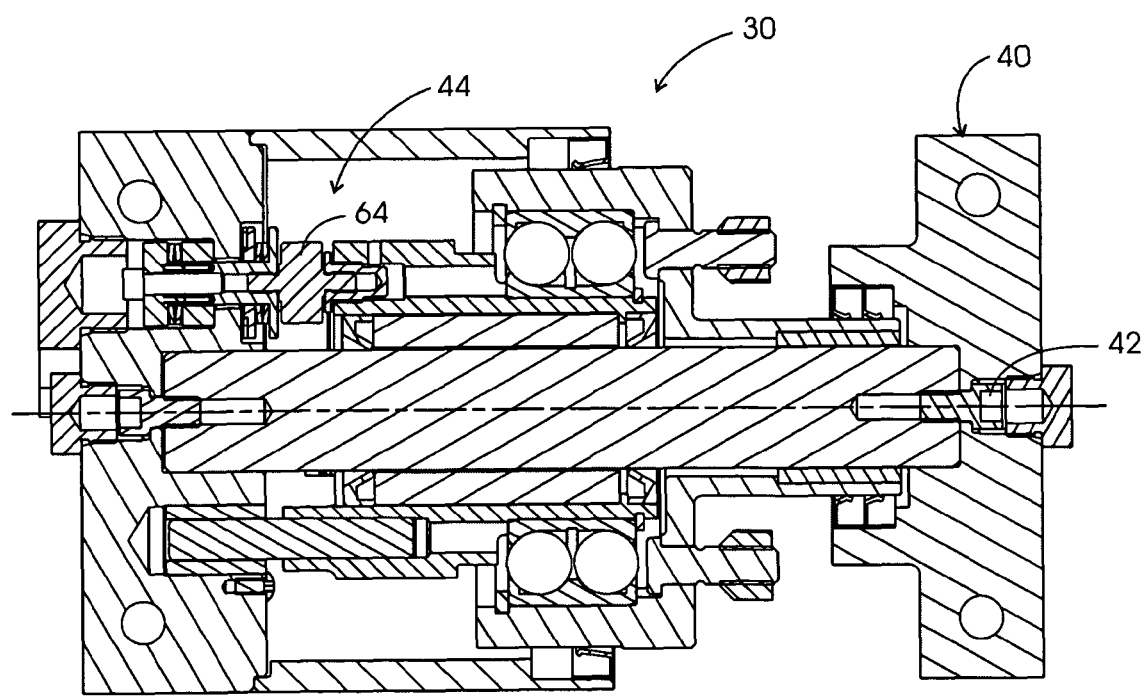
FIG. 14 is a sectional view along line 14-14 of FIG. 3.

As shown in FIG. 14, hub assembly 30 is affixed to frame 14 and houses load cell assembly 44. Most of the automobile hub components (e.g., oil seals, bearings, races, and the like) are standard, such as seen in FIG. 3 of the '098 patent, and will not be described in detail herein. Suffice it to say that load a isolating linear bearing assembly, 146, is integrated into the hub assembly with all but axial forces (loads) being isolated so that load cell assembly 44 measures road surface (frictional) forces, as disclosed herein.

8. Load Cell Bellville/Stop System

An auxiliary wheel mounted to a vehicle can experience relatively high side loads, if the wheel were to be dragged over curbing, etc. It is, thus, necessary to protect the load cell mechanically such that this high loading does not overload the cell beyond its maximum value. A wheel with some small toe angle can be subject to overload forces when the vehicle may catch a curb, etc. An apparent solution may be to increase the capacity of the load cell.

Load cell load resolution enhancement: In order to gain the resolution of force required when using a low force value in the Tow Hitch version illustrated (or the under truck version of the '098 patent), we have incorporated the use of a combination of Bellville washers and load cell in series and then this in parallel with mechanical stops. This is necessary to obtain better load resolution. The Bellville washers are placed in series with the load cell in both the compression and tension directions of load application on the load cell. As load is applied to the cell, the Bellville washers compress as the load cell is measuring the load. Eventually when the load is high enough the mechanical stop comes up against the housing that supports the load cell and, thus, stops any further loading of the load cell, but allowing the load to be taken by the stop. Again, FIG. 4 illustrates the load cell and stop layout.

9. Load Cell Temperature Gradient

The load cell load output value can be affected negatively by having a temperature gradient from one end of the load cell to the other end. If face 'A' happens to be hotter than face 'B' of the load cell, allowing temperature to flow in the axial direction of the cell, during this transition stage whilst the cell is gaining equilibrium temperature the load readings from this cell will be erroneous. The higher the load cell rating the worse will be the affects of this value—typically quoted as a % of full load value. To reduce the transient affects of heat flow to the load cell a temperature inhibitor (titanium in this case) is placed on either side of load cell assembly 44, isolating the cell from the hot and cold faces.

10. Tire Wear Algorithm

Figure 5:
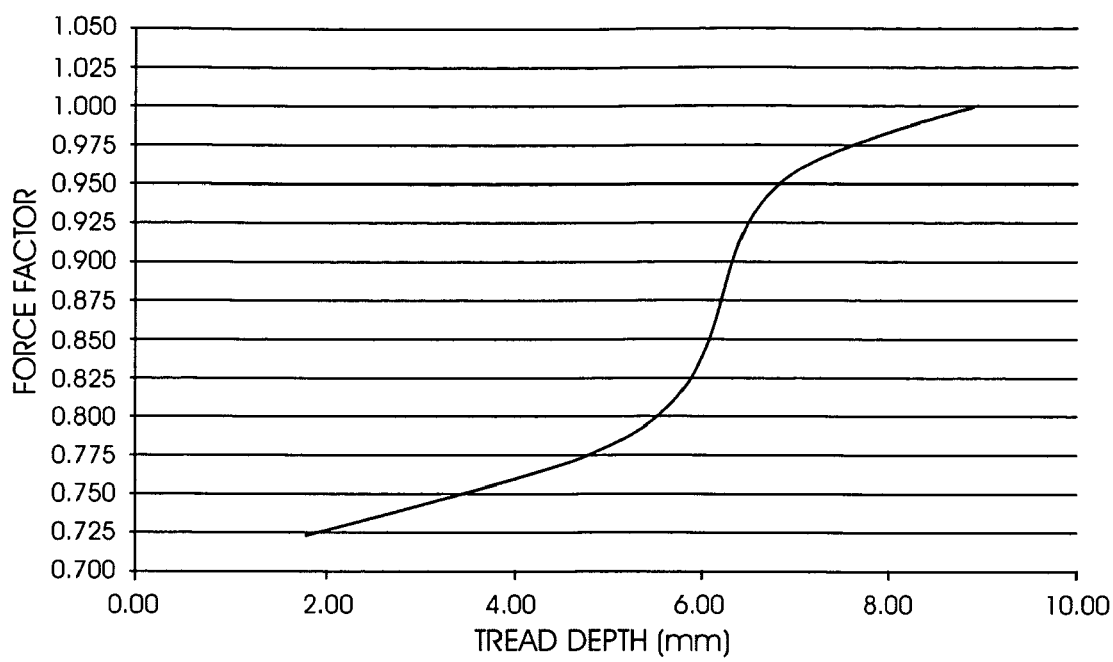
FIG. 5 is a graph of the force factor plotted against the tread depth based on an empirical tire wear algorithm.

With a treaded tire, as the tire wears and the tread depth decreases, the side force between tire and road surface changes. Because of this variation, it is necessary to include compensation for tire wear with mileage, i.e., as the tire wears the measured force is modified by a multiplier factor based on values for the respective tire used. For instance, for a particular tire with a nominal tread depth of 4.0 mm the true force between the tire and the road surface is multiplied by a factor of 0.758 in order to give the corrected friction value on the display. This is performed through an algorithm imbedded in the software within the display. The tire wear algorithm is displayed in FIG. 5, where tread depth (mm) is plotted against the force factor. This algorithm will change depending on the brand of tire used.

11. Tire Distance Measured for Tread Compensation

It also is very desirable to not have to continually enter the tread depth of the auxiliary wheel tire as it wears. Inside the software, is imbedded a tire wear rate algorithm. As long as the tire mileage is measured the tread depth can be calculated. For this reason, inside the GEM force hub is located a rotational displacement sensor which is used in conjunction with the display software to calculate the predicted tread depth and uses this value in its calculation adjustment for tread depth. The software is capable of having the wear rate mileage changed by the operator, since tread wear rate is dependent on the surface over which the tire runs. At any time, the tire tread depth can be measured and the correct tread depth entered into the software.

12. Road/Tire Temperature

Figure 6:
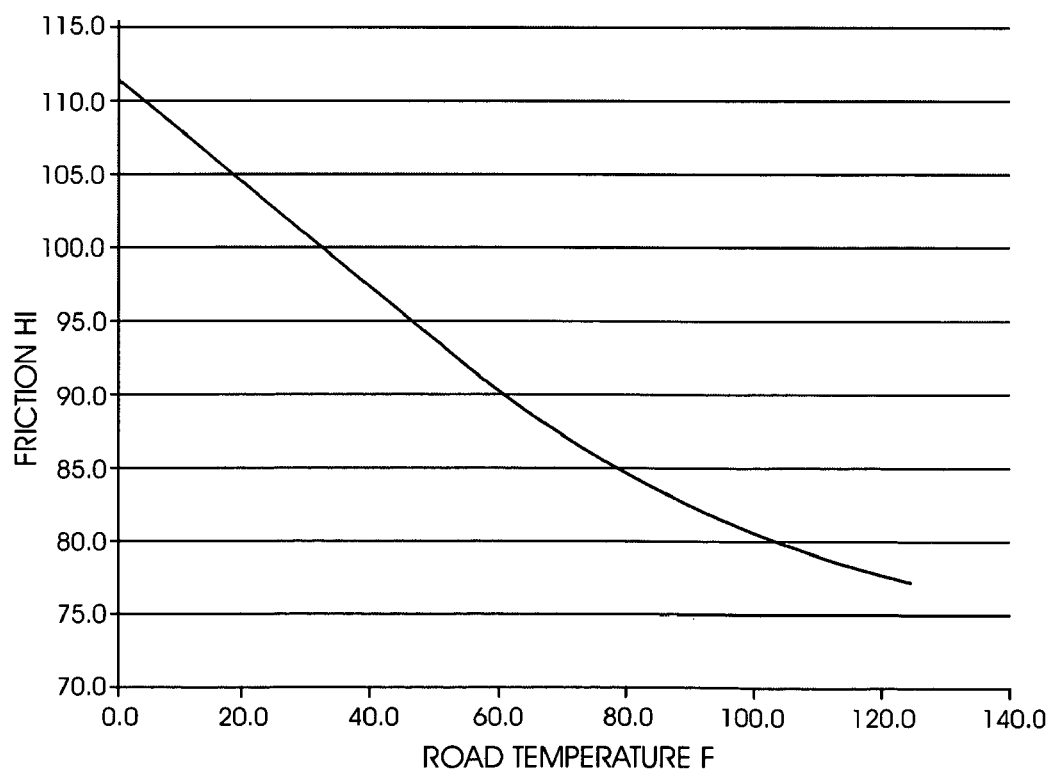
FIG. 6 is a graph of friction plotted against road temperature.

If the road or tire temperature were measured, another adjustment algorithm could be incorporated into the software to allow a compensation of the friction force reading, as is indicated in the FIG. 6 (where road temperature, ° F., is plotted against friction) which shows the variation of friction force generated with variation in road temperature for the particular SE 200 Bridgestone tire used currently. This algorithm would change on the tire being used.

13. RGT Mount Frame Height Adjustment

Figure 7:
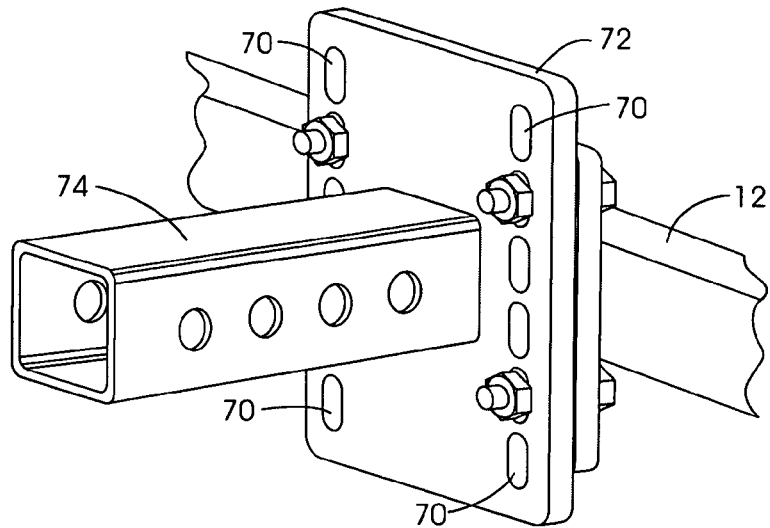
FIG. 7 is an underneath perspective view of the RGT showing the multi slots for variable height position.

The height of the tow hitch varies between vehicles to which the RGT unit is fitted. It is necessary that the RGT mount frame be positioned at a relatively consistent height relative to the ground. For this reason it is necessary to allow for this height change with the central tow hitch being adjustable to the RGT mount frame as shown in FIG. 7. Use of a series of vertical slots, such as a typical slot, 70, permits a hitch plate, 72, carrying the hitch tongue, 74, to be adjusted vertically, which in turn adjusts the vertical height of RGT unit 10.

14. Cantilevered RGT Wheel

Figure 16:
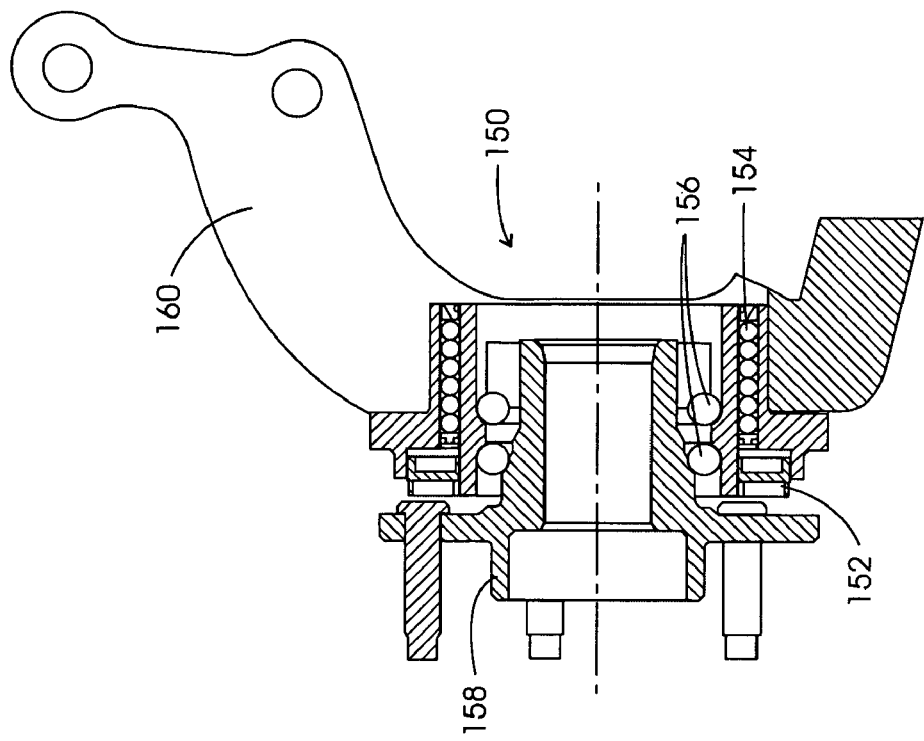
FIG. 16 illustrates yet another way of measuring axial load on the tires where the load cell is designed to remove any rotational forces on the bearings.
Figure 15:
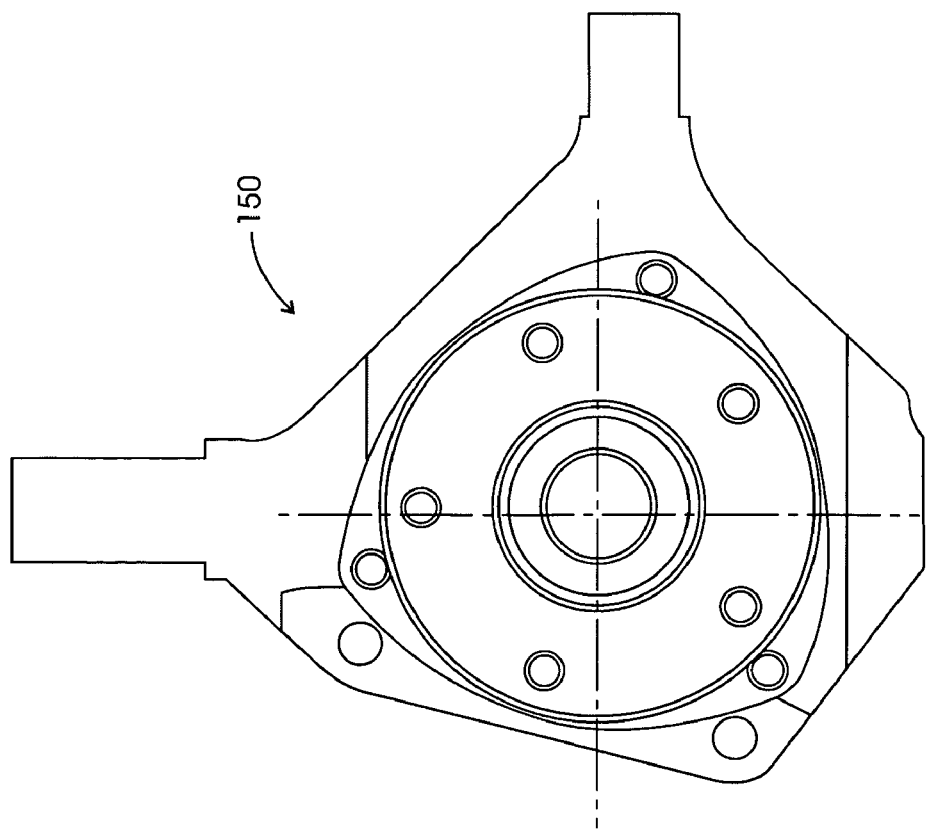
FIG. 15 is a schematic of an alternative placement of the GEM device.
Figure 17:
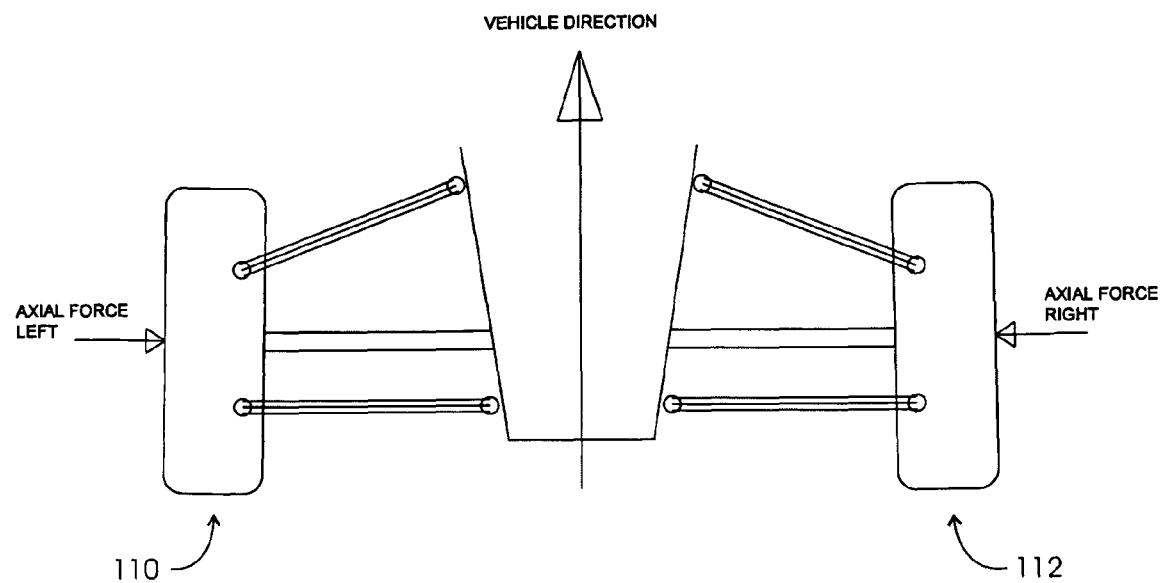
FIG. 17 is an overhead plan view illustrating the permitted installation of the load cell assembly on an ordinary passenger car's front and/or rear wheel center and from this change in force, deduce the friction on the roadway over which the vehicle is traveling.

It is possible, if the RGT wheel has good toe control, to have a fully cantilevered GEM assembly that would allow easy wheel replacement. This would eliminate the need for a swing arm type arrangement. This cantilevered assembly is readily done with the friction load being measured in the GEM hub with a similar arrangement, as shown in FIGS. 15 and 16 for a hub assembly, 150 (this system is one that could be incorporated on any road car to measure the roadway friction as shown in FIG. 17). In FIG. 3, there would not exist any swing arm. The slotted tow adjustment would still be required, however.

The unit illustrated in FIGS. 15 and 16 was mounted on a passenger vehicle and evaluated. RGT assembly 150 includes a load cell assembly, 152, as described elsewhere herein including with reference to FIG. 14; a load isolating bearing assembly, 154; wheel bearings, 156; rotating hub, 158; and steering knuckle, 160.

15. Use of Grip Information

Since the road friction value can be measured in a dynamic mode, it is possible to have a reactive loop feeding from this reading. For instance, the automated deployment of material to the road surface based on the friction reading is possible. An operator, then, can override in case the conditions subjectively referenced are different from the friction measured. For instance with fresh snow on the ground, the operator may wish to plow the snow from the surface before deploying any product. Also, a factor that can affect this is that the product deployment point and the point of friction measurement on vehicles can vary.

16. Steering Affects

Since the friction result is generated by means of a tire being scrubbed along the road at a small tow angle, any steering of the vehicle can change this friction value. As the vehicle steers to the left the friction reading may increase and vice versa when steered to the right. The rate at which this friction force changes can be directly correlated to the amount the vehicle is steered and the speed at which the vehicle is traveling. For this reason, if the steering angle is measured, we can correct in the software with a multiplier for this unwanted friction value change. In its simplest form, the steering input can be used to remove unwanted friction results due to vehicle steering by having the friction result not show any values after a predetermined steering value is achieved in the vehicle in either direction. For either system it would be necessary to calibrate each vehicle steering sensor to the friction display software. The friction correction can be made with the steering input only or with the steering and speed inputs as the multipliers together.

17. Chaining Up RGT Wheel

Figure 8:
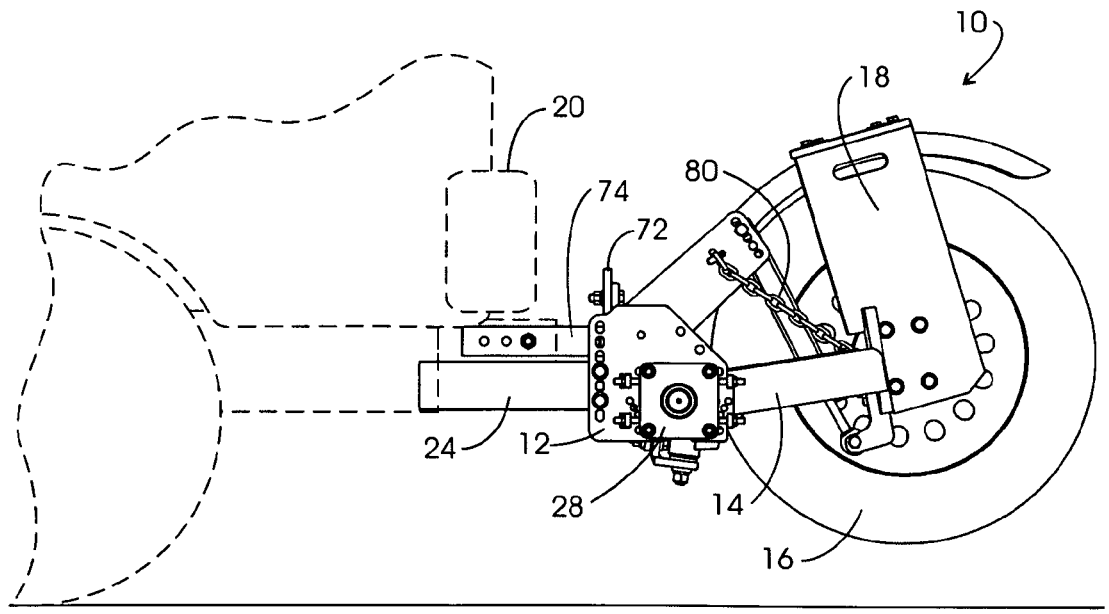
FIG. 8 is a perspective view of the RGT showing the chain holding of the wheel for both the under truck and tow behind versions.

It may be desirable not to run the RGT wheel on the ground for some reason i.e., for example, if one does not wish to wear the RGT out. In this case, it is possible to chain the RGT wheel up off the ground with a chain, 80, as shown in FIG. 8.

18. Alternative Load Cell Placement (Torque Measurement)

When a tire is toed relative to the direction that the vehicle is traveling in plan view the loads between the tire and the road are two fold; an axial force is generated at the axle center and a rotational torque is generated about the center of contact between the road and the tire. Up till now, we have considered how the axial force is measured. We can also measure the result of this torque (which is an indication of friction force between tire and road) by measuring the load on some suspension component (steering tie rod at the front or toe control rod at the rear). It is likely that this load is best measured with a method that encompasses a safety stop system with a high resolution load cell as is used when measuring the axial force. Note that in the RGT system one can replace the GEM hub and place the load cell in any part of the independently supported suspension system where the axial force can be calibrated, i.e., the wheel does not need to be cantilevered to place the load cell elsewhere. In an application where the friction is measured continuously by means of a wheel that is toed relative to the vehicle center, it is possible that the load that is measured can be at an alternate position other than the GEM hub. It is possible that the load cell can be placed within a strut of the support for the friction wheel such that this torque force can be measured and thus calibrated to the friction force between the tire and the road. The leg of the wishbone as indicated in FIG. 17, for example. Through the software, this load measured can be calibrated to the side force reaction load (friction force) between the tire and the road.

19A. Friction Scale (Halliday Friction Number™—HFN™)

Figure 9:
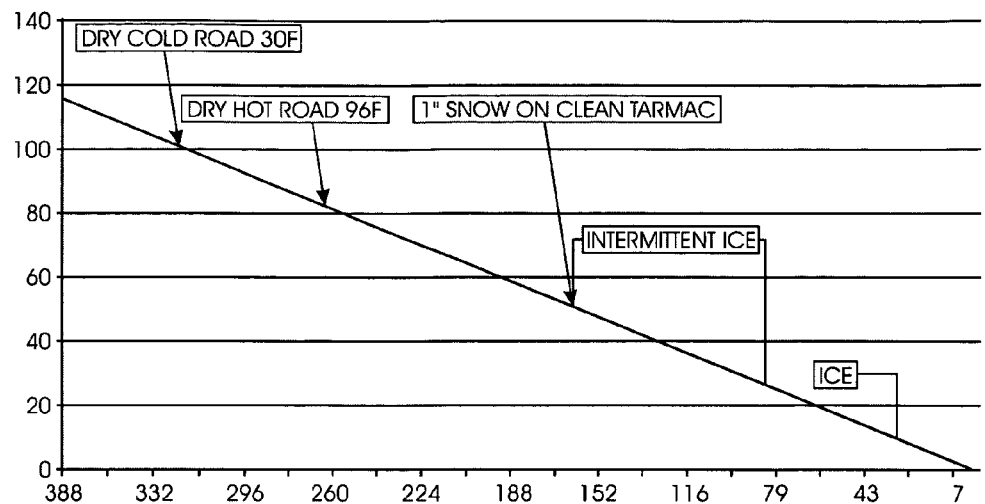
FIG. 9 is graph of the HFN Halliday Friction Scale™ based on an empirical algorithm.

A friction scale is available that references the side force between the tire and the road surface. This scale is a linear relationship between the number and the road surface tire axial side force. That no force between the tire and the road be 0 and that 100 be that side force between the tire and the road when the tire is being run on tarmac that is free from contamination and that the surface be relatively smooth. This value of 100 can be for a road at a particular temperature or it can be a number that is manipulated to take account of the road temperature by using a multiplier as per the temp graph. This is illustrated in FIG. 9, where for plot, 90, the different road conditions are shown for: dry cold road at 30° F., 92; dry hot road at 96° F., 94; 1 inch snow on clean tarmac, 96; intermittent ice, 98; and ice, 100.

Figure 10:
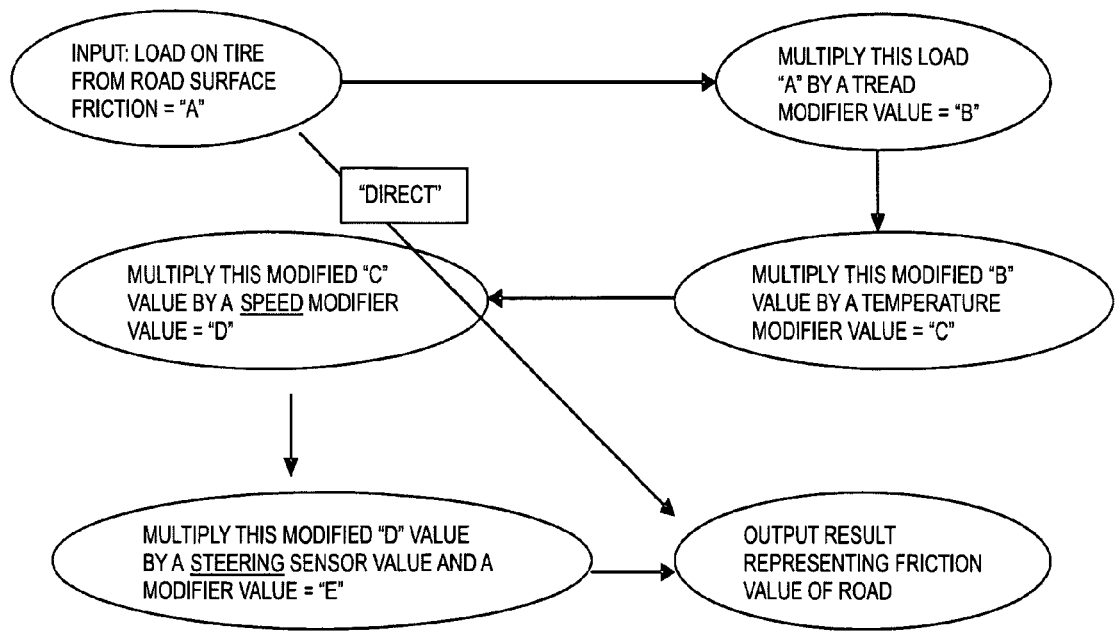
FIG. 10 is flow diagram showing calculation of the empirical algorithm of Applicant's.

Taking into account a tread modifier, a temperature modifier, a speed modifier, and a steering value modifier, the friction value of a road surface can be measured directly or can be mathematically treated with the listed modifiers to derive a friction value of a given road surface, as illustrated in FIG. 10.

19B. RGT Marker Wand

Having a sprung loaded fire hydrant type marker placed on the RGT wheel assembly also is a good idea, because it serves two purposes: the first, being a visual reminder of the presence of the RGT wheel when maneuvering the vehicle; and the second, being a roughness indication of the surface of the road over which the RGT wheel is moving this being indicated by how vigorously the wand is moving.

20. RGT System not Rigidly Mounted to Vehicle Frame

Figure 12:
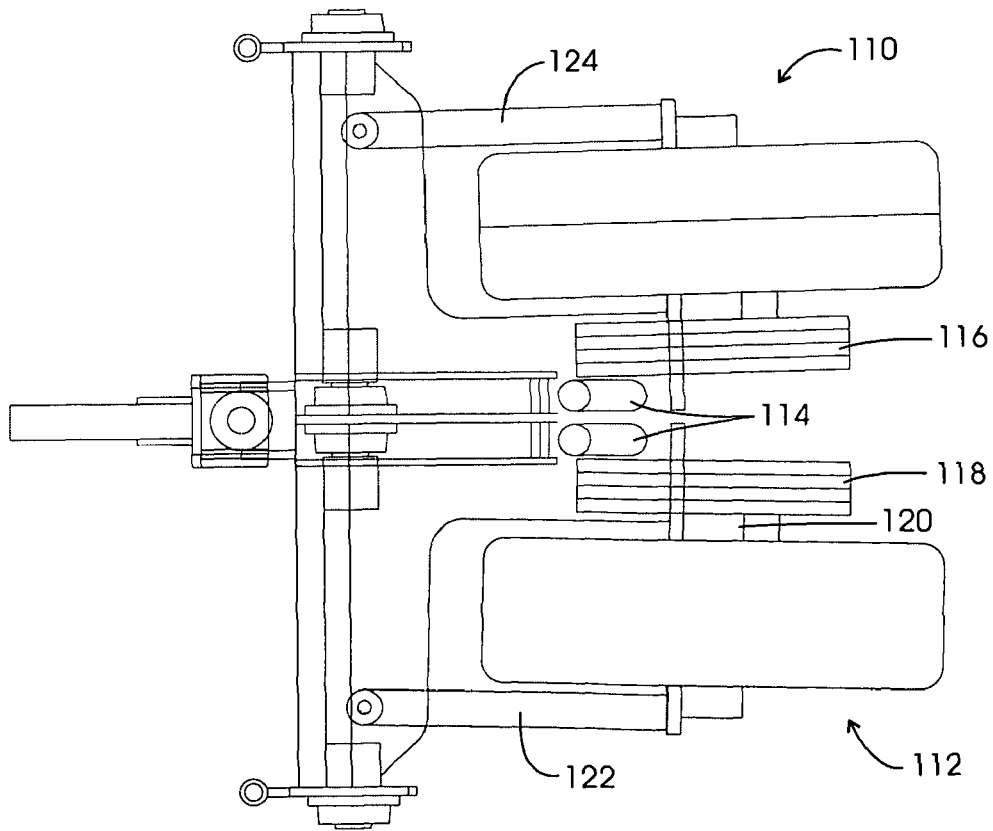
FIG. 12 is an overhead schematic of the tandem wheel arrangement of FIG. 11
Figure 13:
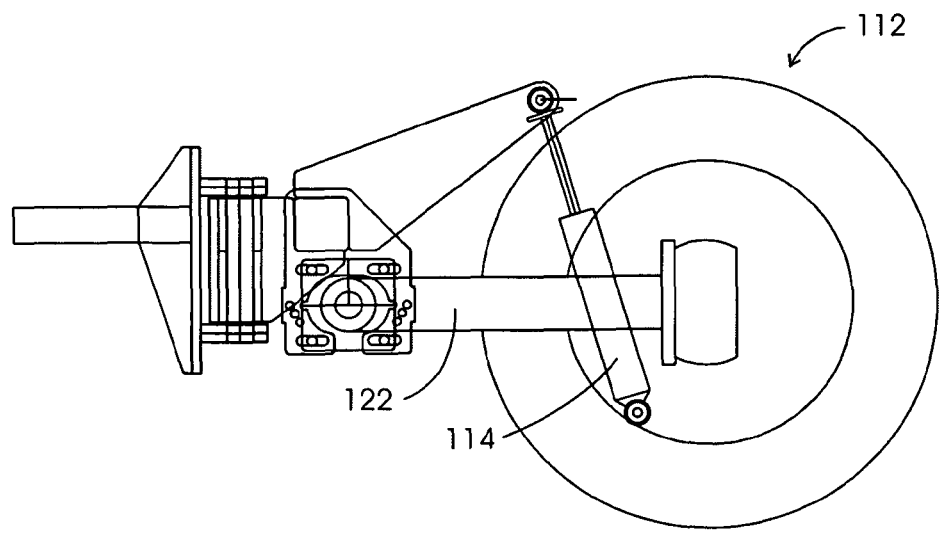
FIG. 13 is a side schematic of the tandem wheel arrangement of FIG. 12.

For general transport and airport use, it is possible that the agency may require a unit that has more accuracy and also has the ability to measure surface friction whilst the vehicle towing the RGT wheel is turning. For this reason, it is possible that a dual wheel system (see FIGS. 12 and 13) could be used within a system that is not rigidly attached to the vehicle frame in the toe alignment direction. This "trailer" system could be toed behind a vehicle with either two separate GEM systems, one for each wheel, or a single GEM system accepting axial loads from each of the two wheels. In either system the net force can be measured and used under all conditions including cornering of the vehicle. This system would allow the road friction whilst cornering to be measured more accurately than with the original GEM system. This system will allow the road friction to be measured around corners. It could be required that for convenience both RGT wheels be capable of being aligned independently of one another relative to the vehicle. With this the force input from a left RGT wheel assembly, 110, and a right RGT wheel assembly, 112, could be averaged to give a net output of grip. This would happen because the right wheel would be toed in/out and the left wheel would be the opposite toe angle. This system would use many of the enhancements of the single wheel RGT unit, as disclosed elsewhere herein.

It also is possible that the two wheels could have their toe angles set relative to one another since the two tires would align themselves relative to the vehicle, as a unit at such an angle to the vehicle whereby the RGT twin wheel unit may be at some small angle relative to the towing vehicle when being driven in a straight line.

It is desirable to place shock absorbing system, 114, at the center of the assembly and adjacent to the ballasts, 116 and 118, such that the shock forces go directly through the twin pivot assembly to the tow vehicle and do not create undesirable force moments on the twin wheel support frame. For ease of backing the unit particularly, one or both sides of the twin wheel frame should be connected to the tow vehicle frame. The RGT unit could be placed on the inside of each wheel assembly with a representative RGT unit, 120, being illustrated in FIGS. 12 and 13. Again, swing arms, 122 and 124, could be used as described herein.

Figure 11:
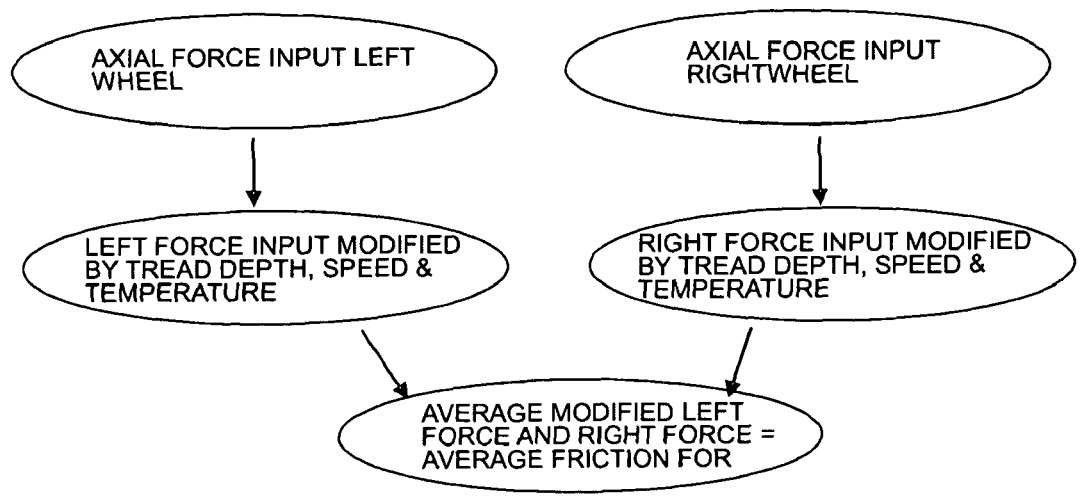
FIG. 11 is a flow diagram showing calculation of average road friction when the RGT is fitted to dual or tandem wheels towed behind a passenger or other vehicle.

The friction value of a given road surface can be determined, for example, by averaging the two values measured for each wheel assembly, such as illustrated in FIG. 11.

B. Safer Car when Used in Slippery Conditions Problem

Many attempts have been made to use the change in speed of a vehicles wheel to indicate roadway friction conditions, i.e. the variation in the high-resolution rotational speed measurement at each wheel. Generally, a vehicle will not experience rotational slip when the vehicle is traveling at relatively constant road speeds (as experienced when in "cruise" mode, for example). This rotational speed variation can very likely be used in association with the vehicles acceleration (or deceleration) to determine road conditions. This condition does not exist when a vehicle is in a non-accelerative mode, for instance, which is a lot of the time in the USA. For this reason, there needs to be some other sensor input that allows the road surface condition to be measured and then indicated to the driver of the car or for the car to be controlled automatically to a safer state.

It is important to realize that a road tire does not transition to rotational slip gradually, i.e., the tire grips or it does not grip in the rotational tractive/braking mode. However, during our investigation of the side forces measured on a road tire, the side or axial force is continually changing as the tire rotates the tire continually grips then lets go as it rotates. For this reason it is far better to use this force variation to determine the surface friction of the road than it is the change in rotational torque indicated by measuring wheel speed difference. This side force as well as continually gripping and letting go also grips with less or more force depending on the surface changing over which it is rolling.

Based on experience of the RGT and GEM inventions, it has become apparent that on any road vehicle the use of side force and tire torque (in plan view) on a tire (any of the vehicle tires, but most likely rear tires) can be used to give to the operator of the vehicle an indication of the friction value between the vehicle tires and the road surface. That is, if one can measure the side load or torque in plan view at each of the rear tires and an algorithm can be created to indicate a direct reference to road friction, then an audible or visual indicator can be directed to the operator of the vehicle to allow the vehicle to be operated with more safety.

With the RGT, a dry road force axial force of 115 lb on a single standard road tire is used to indicate a 'good' friction value and when on an ice surface the friction force falls to a value of approximately 20 lb, i.e., 15% to 20% of the value for dry warm pavement.

The angle of this tire on the RGT is approximately 1.00 degrees to the straight-ahead condition. On a typical car rear tire (for example, a Honda Accord Rear tire) each rear tire is toed in at approximately 0.080" over a 16" distance (rim diameter). This results in an angle of about 0.25 degrees on each rear tire, i.e., ¼ of the angle used on the RGT.

The vertical load on the average rear tire would be higher than the 400 lb used for the RGT. If the load is say 800 lb (some SUV vehicles would be above 1200 lb on each rear corner) and the angle is ¼, it is likely that the tire side load of the SE200 tire is approximately 50 lb on dry road (and greater for a larger tire).

This would result in an ice load of about 10 lb and the car RGT type system would have to have good resolution and mechanical stops to be able to measure the difference between the 50 lb and 10 lb loads predictably and, yet, still be capable of resisting the high side forces experienced by the rear tires of the vehicle.

As with the existing invention with the GEM hub, the car system would need to incorporate a good resolution load cell with mechanical stops with only small axial displacements such that any braking system is not affected negatively. These small axial movements required of this system would require as is standard on most cars, a floating caliper/brake pad system. The anticipated axial movement would only be required to be in the order of ±0.010".

All of the discussion above references to a small vehicle traveling in a straight line whereby the vehicle may have about a 50 lb (dry road) side toe load inward to the vehicle centerline at each rear wheel. This force on each side would drop to about 10 lb; thus, referencing the slippery conditions. These forces are rather low and so an artificial method of increasing these forces should be investigated. Some examples of how this small force can be remedied are indicated below.

It is most likely that for winter conditions that a special winter tire can be used or developed. The special qualities of this tire would be as follows:

More grip at lower temperatures (as is the case with the SE200 Bridgestone)

Be installed on the vehicle in a fixed orientation with a biased tire build that would allow a significantly higher axial load than the estimated 50 lb on dry road (say 100 lb) without negatively affecting the cars handling characteristics.

The Firestone road course rear tire for instance on an Indy type car produces several 100 lb side load pushing to the racecar center, i.e., toe in load and the car handles perfectly OK.

It is also possible that for winter use the rear toe angle can be changed automatically to a more toe in condition for adverse conditions—some of the GM products having active steering at the rear, for example, which cold accommodate such an angle change as a winter mode, possible. Another method for measuring the axial load is illustrated in FIG. 16. Also, this load possibly could be measured within the tire itself and be used in the manner described above. This unit type would be used with the original GEM device.

If this information on friction value is accurately gathered by the vehicle, then it is possible that this friction information can be sent through a phone link ("ON STAR" or other satellite service) to a central group that uses this friction information to indicate by signage to other road users or as can be used with the RGT a direct link to a 'smart sign' such that other vehicles can be directly informed of poor road conditions.

There always is the possibility that a reactive feed back loop can be used directly on the vehicle or externally fed from a central off vehicle station to force the vehicle to travel at a speed appropriate to the conditions, i.e., slower if more slippery.

All 4 corners (or a single corner) of the car can have the axial load or torque in plan view measured and an algorithm can be incorporated to allow the road conditions to be measured as the car corners.

It also is possible to have the road friction condition referenced by just using an axial load measurement off each rear wheel only. The inputs required for this algorithm could include steer angle, vehicle acceleration in any of the three axes, throttle angle (engine torque), gear, and speed.

C. Safer Car—Braking

PROBLEM TO OVERCOME: When braking a vehicle, the driver may apply more or less pressure to the brake pedal in order to stop the car dependent on the requirement of the situation.

In this situation the driver of the car following the vehicle, which is braking, is often unable to see around/through the vehicle doing the braking and/or sense the rate of deceleration of the car and so is unaware soon enough of the braking requirement he has. This inability to sense what the rate of deceleration is of the car ahead is worsened when the conditions and visibility get worse. This I think is one the reasons so often why vehicles crash into one another nose to tail.

When the brake lights come on in the car in front presently it is a single message to the driver behind, i.e., brakes on (lights on) or brakes off (lights off). This signal does not give any degree of deceleration of the vehicle which is slowing other than a sense of the visual deceleration of the vehicle which at times is difficult to sense directly especially in the dark and other adverse driving conditions.

In some newer vehicles, there exist vehicle systems that position a trailing vehicle relative to the vehicle in front by having active proximity sensors to allow this positioning. When in close proximity traffic any sensor of this type may become annoying as most travelers travel too close to the vehicle in front.

It would be advantageous to have a system (possibly light) at the rear of the vehicle that is representative of the degree of deceleration of that vehicle. This can be initiated by an in car accelerometer and/or brake pressure, i.e., the higher the deceleration or braking hydraulic pressure used, the greater the indicator should be the indicator on the rear of that vehicle to the vehicle behind it. Most likely it should be a combination of these two sensors since the vehicle may not be slowing fast enough because it is on a surface that does not have the friction capability. In this case the added input of an activated ABS could trigger this warning to the trailing vehicle.

I suggest that the present brake light system be extended to incorporate a greater number of lights (perhaps 3), i.e., more lights on when the vehicle is slowing at a greater rate and all of the lights on when the vehicle has stopped. Also, it would be possible to have these lights flashing when the deceleration gets beyond a preset value. That is if the deceleration is greater than say 0.5 g then the lights flash as the car is slowing. Alternatively, different color lights green, yellow, red—when all 3 lights are on the greater the deceleration of the vehicle, etc.

Because of the ability of the proximity sensors to control a vehicles position, it also is possible for this following vehicle to measure the rate of deceleration of the vehicle it is approaching and for some type of signal be indicated to the driver of that following vehicle to allow him time to brake his vehicle. This rate of declaration can be linked to the speed of the traveling vehicle and by means of an algorithm associating vehicle speed, rate of approach to the vehicle in front. The vehicle could be decelerated automatically or a series of indicators could be shown the following vehicle driver. The greater the requirement to slow the vehicle the greater should be the indication to slow the vehicle. This indication could be in the form of a series of lights whereby the more lights that are on the greater the requirement to slow the vehicle or as an audible output.

While the invention has been described with reference to various embodiments, those skilled in the art will understand that various changes may be made and equivalents may be substituted for elements thereof without departing from the scope and essence of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims. In this application all units are in the American system and all amounts and percentages are by weight, unless otherwise expressly indicated. Also, all citations referred herein are expressly incorporated herein by reference.

I claim:

1. A method for measuring road surface friction of a road surface using a vehicle that moves across the road surface said vehicle having one or more independently suspended wheel assemblies having an axle and an axle support, which comprises the steps of:
   (a) fitting one or more of each independently suspended wheel assemblies of said vehicle with an assembly that measures axial force between the axle and the axle support of said vehicle; and
   (b) measuring said axial force as said vehicle moves across a road surface; and
   (c) correlating said measured axial force with the road surface friction of said road surface.

2. The method of clam 1, wherein larger measured axial forces correlate with greater road surface friction and smaller measured axial forces correlate with smaller road surface friction.

3. The method of clam 1, wherein said vehicle is driven in a straight line direction, opposite wheel assemblies are fitted with said axial force measuring assemblies, and the measured axial forces are compared to determine the road surface friction.

4. The method of clam 1, wherein toe angle of at least one of said wheel assemblies is set to be greater during winter driving then during summer driving of said vehicle.

5. The method of clam 1, wherein the measured road surface friction is communicated to a driver of said vehicle or to a remote location.

6. A method for signaling a second vehicle driver driving a second vehicle on a road and following a first driver driving a first vehicle on said road, which comprises providing a visual display in said first vehicle to said second driver correlative to the degree to which said first vehicle is decelerating.

7. The method of claim 6, wherein deceleration of said first vehicle is determined by one or more of sensing change in wheel speed, actual sensed values from the change in rotational speed of a wheel, an accelerometer, a decelerometer, or actual sensed values of the brake pressure applied by the first driver.

8. The method of claim 6, wherein said visual display comprises a grouping of lights displayed to said second driver wherein more lighted lights correlates with increased deceleration.

9. The method of claim 6, wherein said visual display comprises a grouping of lights displayed to said second driver wherein different colored lighted lights correlates with increased deceleration.

10. The method of claim 6, wherein the second vehicle is fitted with displacement sensors to determine the proximity of the first vehicle and said first vehicle senses above normal deceleration and that this sensed value of deceleration is used to one or more of visually or audibly indicate to the second driver the rapid closing of the distance between the two vehicles or that this sensed value be used to automatically decelerate the following vehicle.

11. A method for measuring road surface friction of a road surface using a vehicle that moves across the road surface said vehicle having one or more independently suspended wheel assemblies having wheel centers, which comprises measuring the axial force at one or more wheel centers.

12. A method for measuring road surface friction of a road surface using a vehicle that moves across the road surface said vehicle having one or more independently suspended wheel assemblies having an axle and an axle support, which comprises measuring the load on one or more of said struts.

13. A method for measuring road surface friction of a road surface using a vehicle that moves across the road surface said vehicle having one or more independently suspended wheel assemblies having an axle and an axle support, which comprises sensing the torque change (in plan view) by measuring a load on one or more of said struts.

* * * * *